United States Patent [19]

Edwards et al.

[11] Patent Number: 4,867,980

[45] Date of Patent: Sep. 19, 1989

[54] HEAVY DENSITY DEPOT

[75] Inventors: Scott Edwards; Clifford A. A. Graham, both of North Ryde, Australia; Michael T. Shepherd, Berkhamsted, England

[73] Assignee: Coopers Animal Health Australia Limited, South Wales, Australia

[21] Appl. No.: 104,336

[22] Filed: Oct. 2, 1987

[30] Foreign Application Priority Data

Oct. 10, 1986 [AU] Australia .................. PH8436

[51] Int. Cl.$^4$ .............................................. A61K 47/00
[52] U.S. Cl. ..................................... 424/438; 424/468
[58] Field of Search ............... 424/438, 468, 473, 457; 604/891.1

[56] References Cited

U.S. PATENT DOCUMENTS

| | | | |
|---|---|---|---|
| 4,312,347 | 1/1982 | Magoon et al. | 604/891.1 |
| 4,381,780 | 5/1983 | Holloway | 424/438 |
| 4,439,197 | 3/1984 | Honda et al. | 604/891.1 |
| 4,642,230 | 2/1987 | Whitehead et al. | 424/438 |
| 4,671,789 | 6/1987 | Laby | 424/438 |
| 4,675,174 | 6/1987 | Eckenhoff | 424/438 |
| 4,717,718 | 1/1988 | Eckenhoff et al. | 424/438 |

FOREIGN PATENT DOCUMENTS

| | | |
|---|---|---|
| 62164/80 | 3/1981 | Australia . |
| 90108/82 | 5/1983 | Australia . |
| 48082/85 | 12/1985 | Australia . |
| 0062391A1 | 10/1982 | European Pat. Off. . |
| 016241A2 | 12/1986 | European Pat. Off. . |

Primary Examiner—Nancy A. B. Swisher
Attorney, Agent, or Firm—Donald Brown

[57] ABSTRACT

A heavy density depot for lodgement in the remenoreticulum of a ruminant animal and progressive release of veterinary substance, comprises an elongate body containing the veterinary substance and having an aperture to allow its progressive release, and a domed weight at a leading end of the body to facilitate passage down the animal's oesophagus. The weight is usually outside the body. The construction is particularly compact so maximizing the amount of veterinary substance contained.

7 Claims, 3 Drawing Sheets

HEAVY DENSITY DEPOT

The present invention relates to a heavy-density intra-ruminal depot having a compact construction, which is intended to be retained in the rumeno-reticulum of a ruminant animal (e.g. cattle, sheep, etc.).

So called heavy density depots are already known from, for example, Australian Patent specification No. 37281/85. The depot is intended to be passed down the oesophagus of the animal and into the rumeno-reticulum. Once in the rumeno-reticulum, the density of the device causes it to settle in the bottom of the rumeno-reticulum, where it slowly releases a veterinary agent, such as an anthelmintic, a growth-stimulant or ectoparasiticidal agent. If the density of the depot is too low, there is a danger that the depot may be regurgitated from the animal.

U.S. Pat. No. 4,381,780, European Pat. No. 62 391, and Australian patent specification No. 43082/85 show heavy density depots including weights. However, there is unused volume at the ends of the depot which tends to make the depot larger and thus more difficult to administer to the animal.

It is an object of the present invention to provide a heavy density intra-ruminal depot of compact construction, which is easier to administer and allows maximum usage of the available volume for containing the veterinary substance.

Thus, the present invention provides a heavy density intra-ruminal depot, which comprises;

an elongate body containing a solid veterinary substance which is to be progressively released through an aperture in a first end of the body; and a domed weight provided at a second end of the body so as to give the depot a rounded leading end; the depot being of a size and shape capable of passage down the oesophagus into the rumeno-reticulum of an animal, and the weight being such that the overall density of the depot is sufficient to retain the depot in the rumeno-reticulum without regurgitation until the veterinary substance has been substantially completely released.

For ease of administration, the depot has a rounded leading end for passage down the oesophagus. In the present invention, this rounded end is constituted by the domed weight. In order to minimize unused volume, the domed weight generally has a substantially flat trailing end abutting the elongate body. Preferably, the weight will be of hemispherical shape. However, it could also be conical, frusto-conical or other shape suitable to provide the depot with a generally rounded leading end. A "champagne cork" construction, having a substantially hemispherical end and a base portion flaring away to provide a central waisted region, provides a particularly compact weight having good volume utilization.

The weight is preferably formed of a non-toxic metal, such as iron or steel or may be machined, cast, upset or made from powder. Alternatively, the weight may be constituted of metal particles embedded in a polymer matrix.

The weight is generally attached to the outside of the elongate body so that the veterinary substance does not come into contact with the weight. The body may be formed of a plastics material and the weight may be attached thereto by means of integrally molded straps or collars. The collar is usually provided on an inner cylindrical surface of the elongate body and is in snap-fit engagement with a corresponding waisted portion provided around the weight. Alternatively, the weight may be screwed or glued to the body, or attached by means of a central arrow-headed pin. However, it is particularly preferred to provide the weight with suitable internal or external anchoring means (such as corrugated sides, or a flared central bore) and to mould the elongate body of a plastics material around the weight.

The depot can be used with any ruminant animal, including cattle, sheep, goats, deer, camels and buffalo. The overall density of the depot is usually in the region 1.5 to 3.5 g/ml, preferably 2.4 to 3.2 g/ml. It has been found for cattle that a density of at least 2.9 ensures minimal regurgitation of the depot from the rumeno-reticulum or passage further down the alimentary tract. The volume of the depot is chosen dependent on the dose of veterinary agent to be administered, and ease of administration. An upper limit is set by the width of the animal's oesophagus. The overall weight is chosen to provide the appropriate density. For full grown cattle the internal volume is usually 10 to 100 ml, preferably 25 to 50 ml; and for sheep is usually 5 to 50 ml, preferably 10 to 20 ml. For cattle the length is usually 7 to 15 cm, and for sheep is usually 5 to 12 cm.

The elongate body may contain suitable means for progressively releasing the veterinary agent, such as by extrusion of a matrix containing the veterinary agent through an open end of the body under the action of a spring and plunger, as disclosed for example, in Australian patent specification No. 77782/81. If required, the plunger may also be weighted. Alternatively, the veterinary agent could be embedded in a plastics material which slowly erodes once in the rumeno-reticulum. As another alternative, the body itself could be formed of a material which progressively erodes from the first end to expose a matrix material containing the veterinary substance.

To help prevent blockage of the aperture by matter present in the rumen, protrusions such as feet may be provided around the aperture. However, to minimize any possible irritation to the animal it is preferred that the protrusions be rounded or in the form of a cage around the aperture.

The veterinary substance is intended to be slowly released over a prolonged period and generally comprises a veterinary agent uniformly dispersed in a matrix material. The veterinary agent may be a rumen modifier or ionophore which acts as a propionate enhancer to modify the rumen fermentation chemistry (e.g. tetronasin); an anthelmintic such as a benzimidazole, (e.g. oxfendazole, albendazole, thibendazole, triclabendazole, or fenbendazole), a tetrahydropyrimidine (e.g. morantel, or pyrantel), a thiazole (e.g. levamisole, or tetramisole), clorsulon, or an avermectin or milbemycin; a systemic insecticide (e.g. vetrazine); a flukicide such as a salicylanilide (e.q. closantel, rafoxonide, or oxyclosanide); a larvicide (e.g. cyromazin, or vetrazine); an agent to control anoestrus cycling (e.g. melatonin); a polypeptide, growth stimulant, hormone, or other macromolecular particularly in the form of microspheres or nanoparticles; a defaunating agent; an agent to correct dietary deficiency (e.g. trace elements).

Suitable matrixes must be solid (including semi-solid materials) and able to be formed into a stable defined shape. The matrix may be formed of:

(1) Water absorbing substances, which will swell and/or disperse in contact with aqueous fluid systems such as rumeno-reticulum fluid etc. These include bentonite and modified bentonites; gums such as xantham gum or admixtures to control swell and dispersion, carbohydrates and modified carbohydrates, e.g., starch and derivatives thereof; cellulose and modified carbohydrates including esters and ethers thereof, such as methyl or propyl cellulose, carboxymethyl cellulose etc. and admixtures of these with inorganic salts which modify swelling and dispersion of the material, e.g., xantham gum with calcium salts.

(2) Glycols, polyglycols, cross-linked polyglycols, and esters and ethers thereof.

(3) Mono-, di- and polyhydri or alcohols, and ethers or esters thereof, e.g., sucrose monostearate.

(4) Ethylene oxide and/or propylene oxide condensates of (3), e.g., lauryl (dodecanol) condensed with 23 moles of ethylene oxide (available under the trade mark TERIC 12A23).

(5) Polypropylene glycol/polyethylene glycol block co-polymers, and esters and ethers thereof, e.g., those available under the PLURONIC trade mark.

(6) Solid complexes of (1) to (5), e.g., urea complexes.

(7) Degradable polymers, such as polylactic, polyglycollic and polybutyric acids, collagen or modified collagen or admixtures thereof, e.g.

(8) Amino acid polypeptide surfactants, derivatives and salts, e.g., lecithin.

(9) Stearoyl-2-lactylate and salts.

The matrix may be cast or tabletted as appropriate. Embodiments of the present invention will now be described by way of example only with reference to the accompanying drawings wherein.

Figure 1:
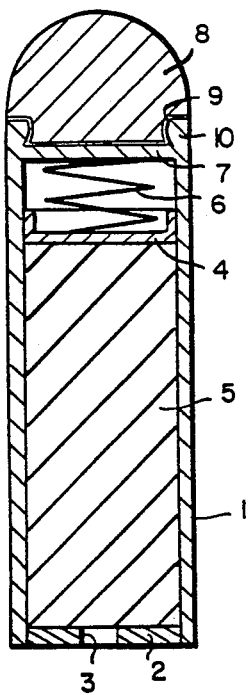
FIG. 1 is a cross-sectional elevation of a heavy density intra-ruminal depot according to the present invention.

The depot of FIG. 1 comprises a cylindrical body 1 formed of plastics material having secured in one end thereof an end plate 2 having a central aperture 3. A plunger 4 is contained in the body to put under pressure a matrix material 5 containing a veterinary agent by means of a coil spring 6 acting on the plunger and an end portion 7 of the body.

A substantially hemispherical steel weight 8 of mass about 60 g is attached to the body at a leading end thereof by means of a groove 9 which engages a complimentary annular bead 10 provided around the periphery of the body. The overall density of the depot is 2.9 g/ml.

The matrix 1 is a sucrose ester, particularly a monostearate ester tablet; or any of the other matrix materials disclosed in International Patent application WO82/00094. The sucrose ester has a particle size greater than 150 microns, which assists flow of the particles and facilitates dry granulation and tabletting. The veterinary agent is uniformly dispersed through the matrix material.

The depot may be used as follows. The depot is administered leading end (i.e. weight 8) first down the oesophagus of the animal until it rests in the rumenoreticulum. Once in the rumeno-reticulum., the fluids present enter through aperture 3 and soften the matrix 5, thereby causing the matrix to be progressively extruded out of the body through the aperture 3 under the action of the spring 6 and plunger 4. The rate of extrusion is controlled by the spring 6 so as to be substantially uniform and to impart a substantially continuous dose of the veterinary substance to the animal over an extended period until all the matrix has been forced out of the body.

Figure 2:
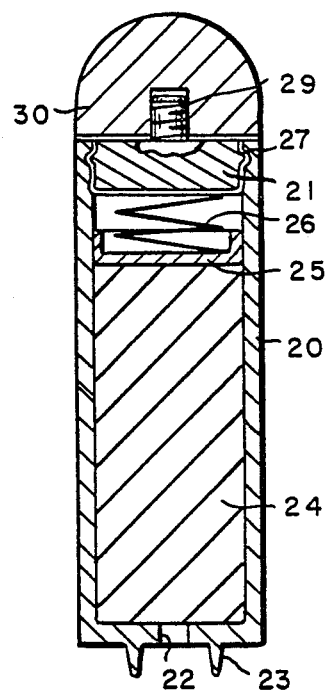
FIG. 2 shows a section of a second embodiment.

FIG. 2 shows a second embodiment which has an integrally molded plastics body 20 with a plug 21 snap fitted into one end. The other end is provided with an aperture 22 for release of the veterinary substance and with integrally molded feet 23 which help to prevent blockage of the aperture by matter present in the rumeno-reticulum. The body contains a solid veterinary substance 24, plunger 25 and spring 26 bearing against the plug.

The plug has a collar 27 which engages a waist 28 provided on the body, and an integrally molded screw 29 which is in screw-threaded engagement with a substantially hemispherical weight 30 which acts as the leading end of the depot.

Figure 3:
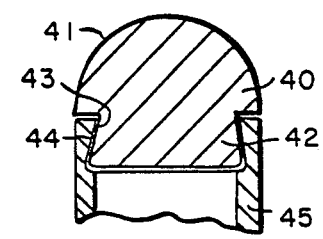
FIGS. 3 to 5 are partial views of third, fourth and fifth embodiments.

FIG. 3 shows a third embodiment having a weight 40 suitable for use with the bodies of either the first or second embodiments. The weight is shaped like a champagne cork and has a hemispherical portion 41 with a flared skirt portion 42 providing a waist 43, which engages a collar 44 provided on the body 45.

Figure 4:
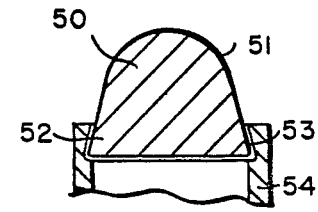

FIG. 4 shows similarly a fourth embodiment having a weight 50 for use with either of the bodies shown. The weight is generally frusto-conical with a rounded portion 51 at the smaller end of the frustum. The wider end 52 is held in a waisted portion 53 provided on the body 54.

Figure 5:
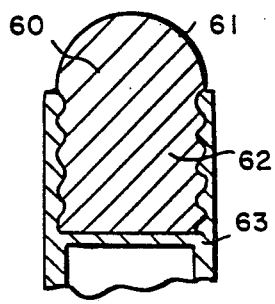

FIG. 5 shows a fi embodiment having a weight 60 for use with either of the bodies shown. The weight has a domed leading end 61 and a corrugated base portion 62 and is made by powder metallurgy techniques. The body 63 is formed of plastics material and is molded around the corrugated portion.

Figure 6:
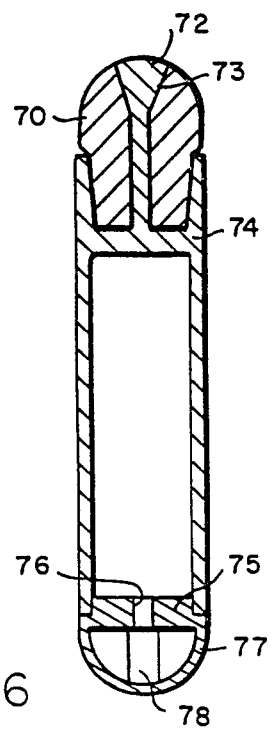
FIG. 6 is a cross-sectional of a sixth embodiment (empty).

FIG. 6 shows a sixth embodiment having a weight 70 attached to body 74 by means of a flared pylon 72 passing through a bore 73 in the weight and integrally molded with body 74 from plastics material around the weight. The depot is shown empty but will contain a spring, plunger and veterinary substance as shown in FIGS. 1 and 2. At the trailing end an end cap 75 is fitted to the body and includes an aperture 76 and a cage 77 formed of integrally molded plastics straps 78 to protect the aperture from becoming blocked by material in the rumen. Such a cage could also be employed in any of the other embodiments.

The claims defining the invention areas follows. We claim:

1. A heavy density intra-ruminal depot for administration down the oesophagus of an animal, which comprises an elongate generally-cylindrical body, the body having a generally-cylindrical interior space containing a solid veterinary substance;

the body further having a first end having an aperture therein and a second end, a spring being provided in the interior space which is resiliently operative between the first end of the body and a plunger abutting the solid veterinary substance;

a domed weight being provided at the second end of the body so as to give the depot a rounded leading end, and comprising a substantially hemispherical leading end and a substantially flat base abutting the second end of the generally cylindrical body such as to minimize unused volume in the depot;

attachment means being provided for attaching the domed weight to the outside of the second end of the body;

the depot being of size and shape capable of passage down the oesophagus into the rumero-reticulum of an animal, and the weight being such that the overall density of the depot is sufficient to retain the depot in the rumeno-reticulum without regurgitation until the veterinary substance has been substantially completely released from the interior space, the solid material being softened in contact with fluids in the rumeno-reticulum and being released from the interior space through the aperture in the first end of the body into the rumeno-reticulum of the animal under the resilient action of the spring operative against the plunger.

2. A depot according to claim 1 wherein the weight is substantially hemispherical with a flared base portion providing a waist.

3. A depot according to claim 1 wherein the weight is substantially frusto-conical with a dome being provided at a narrower end of the frustum.

4. A depot according to claim 1 wherein the weight has a waisted portion which is a snap-fit onto a collar provided on the elongate body.

5. A depot according to claim 1, wherein sides of the weight are provided with anchoring means, and the body is integrally molded from plastics material around the anchoring means so as to attach the weight to the body.

6. A depot according to claim 1 wherein the weight is provided with a central bore flaring outwards at the domed portion of the weight, and the body is integrally molded from plastics material such as to fill the flared bore and so as to attach the weight to the body.

7. A depot according to claim 1 whose density is in the region 2.4 to 3.2 g/ml.

* * * * *